United States Patent [19]

Colas et al.

[11] Patent Number: 5,026,891

[45] Date of Patent: Jun. 25, 1991

[54] CARBOSILANE SURFACTANTS

[75] Inventors: André R. L. Colas, Glashutten, Fed. Rep. of Germany; Franck A. D. Renauld, Barry, Wales; George C. Sawicki, Rixensart, Belgium

[73] Assignee: Dow Corning Limited, Barry, Wales

[21] Appl. No.: 386,068

[22] Filed: Jul. 28, 1989

[30] Foreign Application Priority Data

Aug. 17, 1988 [GB] United Kingdom ............... 8819567

[51] Int. Cl.[5] .................... C07F 7/08; C07F 7/10; C07F 7/18

[52] U.S. Cl. ................... 556/413; 556/404; 556/419; 556/423; 556/428; 556/434; 556/435

[58] Field of Search ............ 556/419, 413, 428, 423, 556/404, 434, 435

[56] References Cited

U.S. PATENT DOCUMENTS 4,777,277 10/1988 Colas et al. ................. 556/419

FOREIGN PATENT DOCUMENTS 1143206 2/1969 United Kingdom ............... 556/419
1198096 7/1970 United Kingdom ............... 556/419
1520421 8/1978 United Kingdom ............... 556/419

Primary Examiner—Paul F. Shaver
Attorney, Agent, or Firm—Jim L. DeCesare

[57] ABSTRACT

Surface active silicone compounds which have an improved stability at a pH above 9 or below 4, have the general formula

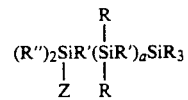

wherein each R independently represents an alkyl or aryl group, each R' represents an alkylene group preferably separating neighbouring silicon atoms by up to 3 carbon atoms, each R" independently denotes R or, only if a is 0, the group $R_3SiR'-$, Z represents a hydrophilic sulphur, nitrogen or phosphor containing substituent or a carboxy-functional group or a salt thereof, and a has the value 0, 1 or 2.

17 Claims, No Drawings

CARBOSILANE SURFACTANTS

This invention relates to silalkylene compounds, which are also known as carbosilanes, and to the use of such compounds as surface active materials.

Surface active organosilicon compounds have been known for some time and include such materials as organopolysiloxane polyoxyalkylene copolymers and sulphonate functional polysiloxanes. G.B. Patent Specification No. 1 198 096 for example describes a polysiloxane having 0.1 to 100 mole percent of units of the formula

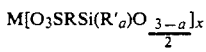

wherein M is a cation, R' is a certain monovalent group and R is a certain hydroxy-substituted divalent group where the hydroxy substituent is bonded to a carbon atom vicinal to which the $-O_3S-$ group is bonded, a is 0, 1 or 2 and x is 1, 2, 3 or 4 and is equal to the valency of said cation, and 0.0 to 99.9 mole percent of units of the formula

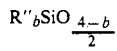

wherein R" is hydrogen or a monovalent group as for R', and b is 1, 2 or 3. Said polysiloxanes are stated to be useful for example in the production of emulsions for use in making polishes, of treating baths of increased wetting properties and of media having increased surface activity.

In G.B. Patent Specification No. 1 143 206 there are described organopolysiloxane polyoxyalkylene copolymers having the general formula wherein Me denotes a methyl group $Me_3SiO(Me_2SiO)_q[H(OC_2H_4)_x(OC_3H_6)_yO(CH_2)_zSiMeO]_pSiMe_3$ in which q has a value from 3 to 25, x has a value from 1 to 25, y has a value from 0 to 15, z is 2 or 3, p has a value from 1 to 10, at least 25 percent by weight of the oxyalkylene groups being oxyethylene.

Organosilicon compounds of the types described above are, however, not suitable for use under acidic and basic conditions due to a catalysed cleavage of Si—O—Si bonds.

G.B. Patent Specification No. 1 520 421 describes organosilicon compounds represented by the general formula

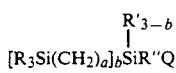

in which each R represent a methyl, ethyl, propyl or trifluoropropyl radical, R' represents an alkyl radical having up to 6 carbon atoms, R" represents a divalent aliphatic hydrocarbon radical having 2 to 6 carbon atoms, Q represents $-O(C_2H_4O)_cX$ in which c has a value of from 3 to 12 and X represents H, R''', $-C(=O)R'''$ or $-C(=O)OR'''$ in which R''' represents an alkyl radical, a is 1 or 2 and b is 2 or 3. Such compounds, though more stable in alkaline and acid conditions than the above mentioned silicone compounds, are not very stable in extreme acidic conditions due to the catalysed cleavage of ethylene oxide units. The surface tension of the materials exemplified in G.B. Patent Specification 1 520 421 in 1% aqueous solutions is above 26 Dyne/cm.

There is, therefore, a continuing search for materials with improved surface activity and which have also an improved stability in alkaline and acid conditions.

The invention provides in one of its aspects organosilicon compounds represented by the general formula

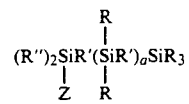

wherein each R independently represents an alkyl, aryl, halogenated alkyl or halogenated aryl group having up to 18 carbon atoms, each R' represents an alkylene group, separating neighbouring silicon atoms by up to 6 carbon atoms, each R" independently denotes R or, when a is 0, may also denote the group $R_3SiR'-$, Z represents a hydrophilic substituent containing sulphur, nitrogen, phosphorus or a carboxy-functional group or a salt of said carboxy group, and a has the value 0, 1 or 2.

In the general formula of the organosilicon compounds of the invention R may be for example methyl, ethyl, isopropyl, isobutyl, phenyl, dodecyl, octodecyl or trifluoropropyl. It is preferred that at least 50%, preferably at least 80% of all R groups are methyl groups. R' may be e.g. methylene, dimethylene, isobutylene, n-propylene, isopropylene, pentylene, neo-pentylene or hexylene. Preferably 1 to 3 carbon atoms separate the silicon atoms and most preferably R' is methylene or ethylene. R" may be R as defined above, and in the case of a being 0 may alternatively be a group of the formula $R_3SiR'-$, wherein R and R' are as defined above. If a is 0 it is preferred that only one R" denotes an $R_3SiR'-$ group. Preferably a is 0. Z is a group which has hydrophilic character which contains S, N or P or a carboxy-functional group or a salt thereof. Such groups include for example those containing sulphonate, sulphosuccinate, acid amide, sarcoside, alkanolamine, alkanolamide, alkylisothionate, phosphate, betaine, quaternary ammonium salt, amphoteric groups, zwitterionic groups, carboxyl groups or sulphate groups. The preferred Z groups are those that contain a sulphonate, carboxyl group or zwitterionic group or a quaternary ammonium salt.

The functional groups Z may be linked directly or indirectly to a silicon atom. Preferably the Z group has the general formula YQ, wherein Y denotes a divalent group, consisting of H, C. and optionally N or oxygen, and Q is the functional unit which may be for example a sulphonate group with a cation. Examples of the Y group include n-butylene, o-xylylene, ethyl-propyl-dimethylammonium andpropylene. Examples of Q groups are $-SO_3^-Na^+$, $-COOH$, $-N^+(CH_3)_2-O^-$ and $-N^+(CH_3)_3I^-$.

The silicone compounds of the invention may be prepared according to a process which comprises reacting compounds comprising hydrophilic substituents, with suitable silalkylene compounds.

The invention provides in another of its aspects a method of making organosilicon compounds of the general formula

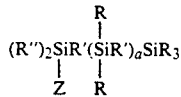

which comprises reacting together a hydrophilic substituent containing compound Z' with a silalkylene compound of the general formula

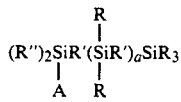

wherein R, R', R" and a are as defined above and A denotes a hydrogen or a reactive group and Z' denotes a group such that upon reaction of A with Z' the group Z is formed.

The group Z' preferably has the general structure A'Q, wherein Q is as defined above and A' is a group which upon reaction with A forms the group Y as defined above. If the group A is a hydrogen atom the silalkylene compound may be reacted with a compound Z' which has an unsaturated group in the presence of an addition reaction catalyst, for example a Pt containing compound. Such compounds Z' may have the general formula A'Q wherein A' is an allylene or vinylene group and Q is as defined above. If the group A is an amino-functional group, for example an aminoalkylene group, Z' may be an acid anhydride, e.g. maleic anhydride, a sultone e.g. propane sultone, hydrogen peroxide, a haloalkane, e.g. iodomethane or a halocarbinol, e.g. iodoethanol. If A is an epoxy-functional group e.g. propyl glycidyl ether or contains a carboxylic group Z' may be a sulphite, e.g. Na metabisulphite. These examples are not exhaustive and the personn skilled in the art will be able to find manysimilar reaction mechanisms to produce the organosilicon surfactants of the inentin. These reactions are preferably carried out in a mixture of solvents, e.g. comprising tetrahydrofuran, toluene or methanol. The reagents used will be dtermined by the type of surface active material desired.

The silalkylene starting material for the method of the invention may be obtained by known methods, e.g. those described in "Chemistry and Technology of Silicones" by W. Noll. Thse include the condensation of chloroalkylsilanes with chlorosilanes or other chloroalkylsilanes, by means of electron donating metals, for example Na, Li, K, Mg and Zn, according to the reaction ≡SiXCl+Cl—Si≡→≡Si—X—Si≡. Another reaction is the hydrosilylation of silicon compounds having aliphatically unsaturated substituents, in the presence of addition reaction catalysts, e.g. Pt ≡Si—H+CH$_2$=CH—(X)$_b$—Si≡→≡Si—CH—CH—(X-)$_b$—Si≡ wherein X is a divalent alkylene group, and b is 90 or 1. In order to make the silalkylene materials more reactive with the compounds comprising hydrophilic compounds, it is preferred to ensure the prsence of a reactive substituent on the silalkylene compound. Such reactive substituents are for example amino groups or epoxy groups which are substituted onto the silalkylene e.g. by reacting unsaturated amines or epoxy groups with silicon-bonded hydrogen atoms.

The silalkylene compunds of the inventin are useful as surfactants. Their surface tension in water is as low as 23 to 25 dyne/cm. They are alostable in conditions where the pH exceeds 9 or falls below 4. The prefered compounds are stable at very low pH valus. The more conventional surface active materails based on silicone compounds break down at both higher and lower pH values.

Of the following examples in which all parts and percentages are expressed by weight and Me deontes a methyl group, examples 5 to 15 illustrate the invnetin while examples 1 to 4 describe the preparation of the starting materials.

EXAMPLE 1

A 500 ml three neck flash fittd with a condenser, nitrogen inlet, dropping funnel and stirrer was charged with 12.2g (0.5 mole) of magnesium pellets and 100ml of diethyl ether. The Grignard reaction was initiated at reflux with dibromoethane and carried out by slow addition of 61g (0.5 mole) of chloromethltrimethyl silane. After complete addition 28.7g (0.25 mole ) of dichloromethyl silane were slowly added with 70ml of tetrahydrofuran and the mixture was refluxed for 5 hours. Work up with water and distillation gave the corresponding bis(trimethylsilyl methyl)methyl silane in 90% yield.

EXAMPLE 1a

A 500ml three neck flash fitted with a condenser, nitrogen inlet, dropping funnel and stirrer was charged with 20g (0.81 mole) of magnesium pellets and 150ml of dry tetrahydrofuran. The Grignard reaction was initiated at reflux with iodine and dibromoethane adn carried out by slow addition of 100g of chloromethyltrimethyl silane. After complete addition 33.8g (0.25 mole) of trichloromethyl silane were slowly added at a temperature close to 60° C. After addition 300ml of tetrahydrofuran were added and the mixture was refluxed for 4 hours. Work up with water and distillation gave the corresponding tris(trimethylsilyl methyl) silane.

EXAMPLE 1b

A 500ml three neck flash fitted with a condenser, nitrogen inlet, dropping funnel and stirrer was charged with 12.2 g (0.5 mole) of magnesium pellets and 100 ml of dry diethyl ether. The Grignard reaction was initiated at reflux with iodine and dibromoethane and carried out by slow addition of 61.2g (0.05 mole) of chloromethyltrimethyl silane at a temperatureof 36° C. After complete addition 47.2 g(0.05 mole) of chlorodimethyl silane were slowly added. The exothermic reaction was maintained at reflux temperature for 2 hours. Work up with water and distillation gave the corresponding pentamethyl disilmethylene.

EXAMPLE 1c

A 1 liter flask fitted with a condenser, dropping funnel, nitrogen inlet, thermometer was charged with 12.15g (0.5 mole) of magnexium and 50ml of diethl ether. The reaction was initiated withiodine at reflux. 97.2g(0.5 mole) of 1-chloromethyl 1,1,2,2,2-pentamethyl disilmethylene were then slowly added to maintain a pot temperature of 35 to 40° C. After complete addition 47.2g (0.5 mole) of chlorodimethylsilane in 100ml of diethylether were slowly added (exothermic reaction) to obtain a pot temperature of 40 to 45° C. After complete addition the mixture was stirred for 1 hour at 50° C. Work up with water and distillation gave 99g of Me$_3$Si(CH$_2$SiMe$_2$)$_2$H.

EXAMPLE 2

A 100ml flask fitted with a condenser, dropping funnel, nitrogen inlet and stirrer was charged with 8g (0.07 mole) of allyl glycidyl ether. The falsk was heated to 90° C. and 0.05ml of a 10% solution of chloroplatinic acid in isopropyl alcohol was added. When heated up to 115° C. 13g (0.06 mole) of bis(trimethylsilyl methyl)-methyl silane, as prepared in Example 1, were slowly added. When the reaction was completed volatiles were removed under reduced pressure and a product was distilled at 2mm Hg and 138 to 140° C. with the formula

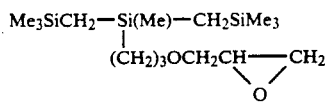

EXAMPLE 2a

A 100ml flask fitted with a condenser, dropping funnel, nitrogen inlet and a thermometer was charged with 20g (0.091 mole) of Me$_3$Si(CH$_2$SiMe$_2$)$_2$H as prepared in Example 1c. The flask was then heated to 90° C. and one drop of platinic acid was added (10% in IPA). The temperature was then brought to 96° C. and 11.4g (0.1 mole) of allyl glycidyl ether were slowly added (exotherm). After complete addition the mixture was heated to 100° C. for 10 minutes and distilled to afford the corresponding epoxy functional carbosilane

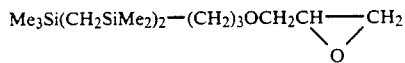

EXAMPLE 3

A 100ml flask fitted with a condenser, dropping funnel, nitrogen inlet and stirrer was charged with 20g (0.092 mole) of bis(trimethylsilyl methyl)methyl silane as prepared in Example 1. The flask was heated to 77° C. and 0.05ml of a 10% solution of chloroplatinic acid in isopropyl alcohol was added. When heated up to 110° C, 13g (0.1 mole) of allylamine, which was silylated with a trimethylsilyl group, were slowly added. When the reaction was completed the mixture was cooled to 20° C. and 50ml of ethanol were added to remove the silylation from the amino group. The mixture was stirred for 30 minutes at 60° C. after which distillation at 2mm Hg at 102 to 106° C, gave a carbosilane with the formula

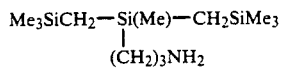

EXAMPLE 4

A 100ml flask fitted with a condenser, dropping funnel, nitrogen inlet and stirrer was charged with20g (0.092 mole) of bis(trimethylsilyl methyl)methyl silane, as prepared in Example 1, and 8 g (0.095 mole) of N-dimethyl allylamine. The flask was heated to 80° C. and 0.05 ml of a 10% solution of chloroplatinic acid in isopropyl alcohol was added. An exothemic reaction took the temperture up to 106° C. Whenheated up to 130° C. for 30 minutes, the reaction was completed. Distillation at 5mm Hg and 110 to 120° C., gave a carbosilane with the formula

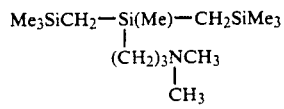

EXAMPLE 4a

A 250ml flask fitted with a conenser, dropping funnel, nitrogen inlet and stirrer was charged with 50g of tris(-trimethhlsilyl methyl) silane, as prepared in Example 1a, and 16.15g of N-dimethyl allylamine. The flask was heated to 91° C. and 0.05ml of a 10% solution of chloroplastinic acid in isopropyl alcohol was added. When heated up to 110° C. for 4 hours, the reaction was completed. Distillation at 2mm Hg and 115 to 123° C., gave a carbosilane with the formula

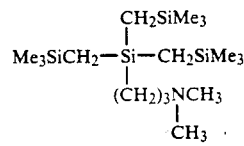

EXAMPLE 4b

Using a similar procedure to Example 4a, but starting from pentamethyl disilmethylene, a carbosilane was made with the formula

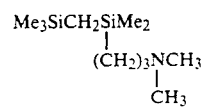

EXAMPLE 4c

A 250ml flask fitted with a condenser, dropping funnel, nitrogen inlet, thermometer was charged with 63.3g (0.29 mole) of Me$_3$Si(CH$_2$SiMe$_2$)$_2$H as prepared in Example 1c. The flask was heated to 75° C. and 2 drops of chloroplatinic acid (10% in IPA) were added. 27.2g (0.32 mole) of N-dimethyl allyl amine were slowly added. Exothermic reaction occurred (up to 105° C). After complete addition the mixture was heated to 110° C. for 30 minutes and distilled to afford the corresponding adduct

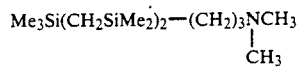

EXAMPLE 5

6g of epoxy functional bis(trimethylsilyl methyl) methyl silane as prepared in Example 2, were dissolved in 14g of ethanol and 2g of water. The solution was heated to reflux, 1.71g of sodium metabisulphite and 0.23g of sodium sulphite were added in 10g of water. The mixture was kept under reflux for 10 hours, filtered and volatiles were removed at reduced pressure. This resulted in a white solid of the general formula

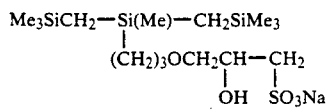

EXAMPLE 5a

A 250ml flask fitted with a condenser, dropping funnel, nitrogen inlet and a thermometer was charged with 27g (0.081 mole) of epoxy functional carbosilane as prepared in Example 2a, 54g of ethanol and 14g of water. The mixture was then heated to 63° C. and 7.85g (0.041 mole) of sodium metabisulphite with 0.8g of sodium sulphite dissolved in 48g of water were slowly added. After complete addition the mixture was heated to 75° C. for 10 hours. Filtration and stripping afforded a white solid which was dissolved in ethanol and precipitated with acetone to yield the corresponding sulphonate carbosilane as a white hygroscopic solid with the formula

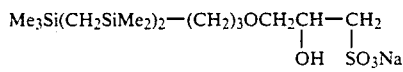

EXAMPLE 6

A 100ml flask, fitted with a condenser, nitrogen inlet, dropping funnel and stirrer was charged with 6.5g (0.023 mole) of aminopropyl functional carbosilane, as prepared in Example 3. 6.5g of maleic anhydride dissolved in 10g of toluene were then carefully added so that the pot temperature did not exceed 25 to 30° C. After complete reaction the mixture was heated to 50° C. for 15 minutes and stripped, resulting in the compound of the formula

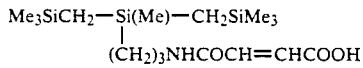

of which 8.5g were charged to a flask, diluted in 8g of methanol. About 20ml of N sodium hydroxyde solution were added to raise the pH to 8 and 1.9g of sodium metabisulphite were added. The mixture was refluxed for 2.5 hours filtered and stripped to afford as a white powder, the sulphosuccinate carbosilane of the formula

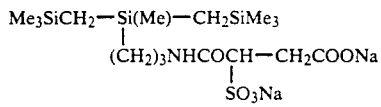

EXAMPLE 7

A 100ml flask fitted with a condenser, dropping funnel, nitrogen inlet and stirrer was charged with 12.9g (0.042 mole) of N-dimethyl aminopropyl carbosilane, as prepared in Example 4, dissolved in 15g of toluene, together with 5.9g (0.045 mole) of 1.3 propane sultone. The mixture was slowly heated to 80° C. over a period of 90 minutes. Volatiles were stripped off at reduced pressure and a viscous oil was obtained of the general formula

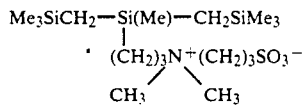

EXAMPLE 7a

A 250ml flask fitted with a condenser, dropping funnel, nitrogen inlet and stirrer was charged with 7.5g (0.02 mole) of N-dimethyl aminopropryl carbosilane, as prepared in Example 4a, dissolved in 7.5g of toluene together with 2.45g (0.02 mole) of 1.3 propane sultone. The mixture was slowly heated to 90° C. over a period of 2 hours. Volatiles were stripped off at reduced pressure, and a compound was obtained of the formula

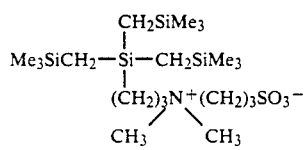

EXAMPLE 7b

A similar procedure was used as described in Example 7a, starting from the carbosilane produced according to Example 4b, giving a compound of the formula

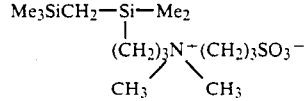

EXAMPLE 7c

A 100ml flask fitted with a condenser, nitrogen inlet and thermometer was charged with 20.0g (0.066 mole) of N-dimethyl aminopropyl carbosilane, as prepared in Example 4c, 8.0g (0.066 mole) of propane sultone and 20g of toluene. The mixture was then stirred at room temperature and a slight exotherm noted (26° C). The solution was then heated to 81° C. for 2 hours and poured in 100ml diethylether. The sulphobetaine was then obtained by precipitation and filtration. The resulting solid was dried under vacuum and has the formula

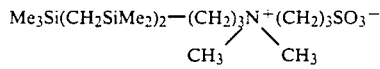

EXAMPLE 8

A 100ml flask fitted with a condenser, dropping funnel, nitrogen inlet and stirrer, was charged with 5g of methanol and 3.6g of H₂O₂ (30% in water). The flask was heated to reflux and 10.1g of N-dimethyl aminopropyl carbosilane, as prepared in Example 4 were added. The mixture was refluxed for 4 hours. Volatiles were stripped off at reduced pressure, and a clear viscous oil was obtained of the general formula

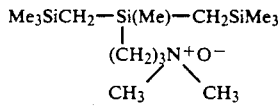

EXAMPLE 8a

A 250ml flask fitted with a condenser, dropping funnel, nitrogen inlet and stirrer was charged with 5g of methanol and 3.5g of H$_2$O$_2$ (30% in water). The flask was heated to reflux and 9.37g of N-dimethyl aminopropyl carbosilane as prepared in Example 4a were added. The mixture was refluxed for 4 hours. Volatiles were stripped off at reduced pressure and a clear viscous oil was obtained of the general formula

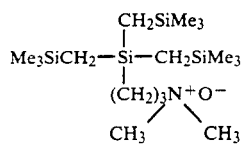

EXAMPLE 8b

A similar procedure was used as described in Example 8a, starting from the carbosilane produced according to Example 4b, giving a compound of the formula

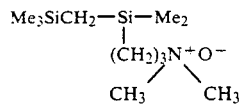

EXAMPLE 8c

A 100ml flask fitted with a condenser, nitrogen inlet and thermometer was charged with 20.0g (0.066 mole) of N-dimethyl aminopropyl carbosilane, as prepared in Example 4c and 10ml of methanol. The solution was heated to 55° C. and 8.2g of hydrogen peroxide (0.072 mole) (30% in H2O) were slowly added. After complete addition the mixture was heated to 61° C. for 2 hours and stripped under reduced pressure to yield a colourless oil corresponding to the N oxide carbosilane of the formula

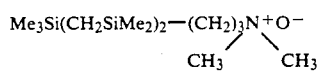

EXAMPLE 9

A 250ml flask fitted with a condenser, dropping funnel, nitrogen inlet and stirrer was charged with 7.75g (0.055 mole) of iodomethane and 15g of tetrahydrofuran. 15g (0.05 mole) of N-dimethyl aminopropyl carbosilane as prepared in Example 4 were added in 20g of tetrahydrofuran. The mixture was then heated to 40° C. for 30 minutes. Volatiles were stripped off at reduced pressure and a white solid was obtained of the general formula

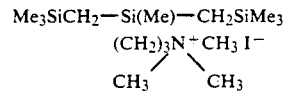

The chloride derivative was obtained by cation exchange by equilibration with a 5% solution of NaCl in water.

EXAMPLE 10

A 250ml flask fitted with a condenser, dropping funnel, nitrogen inlet and stirrer was charged with 9.46g (0.055 mole) of iodoethanol and 25g of tetrahydrofuran. 15g (0.05 mole) of N-dimethyl aminopropyl carbosilane as prepared in Example 4 were added in 25ml of tetrahydrofuran. The mixture was then heated to 63° C. and refluxed for 60 minutes. Volatiles were stripped off at 90° C. under reduced pressure and a yellow solid was obtained of the general formula

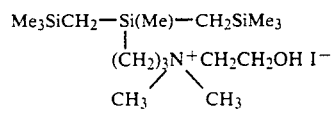

EXAMPLE 10a

A 250ml flask fitted with a condenser, dropping funnel, nitrogen inlet and stirrer was charged with 3.44g (0.02 mole) of iodoethanol and 7.5g of dry tetrahydrofuran. 7.5g (0.02 mole) of N-dimethyl aminopropyl carbosilane as prepared in Example 4a were added. The mixture was then heated to 60 to 65° C. and refluxed for 4 hours. Volatiles were stripped off under reduced pressure and a compound was obtained of the formula

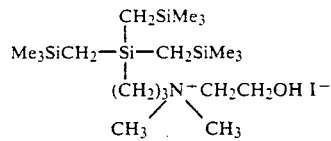

EXAMPLE 10b

A similar procedure was used as described in Example 10a starting from the carbosilane produced according to Example 4b giving a compound of the formula

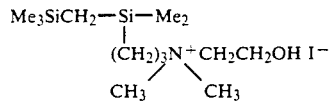

EXAMPLE 10c

A 100ml flask fitted with a condenser, nitrogen inlet and thermometer was charged with 20.0g (0.066 mole) of N-dimethyl aminopropyl carbosilane, as prepared in Example 4c, 20ml of dry tetrahydrofuran and 11.35g (0.066 mole) of iodoethanol. The mixture was then heated to 72° C. for 4 hours and poured in 100ml diethylether. The corresponding quaternary ammonium was so obtained by precipitation, filtrated and dried under vacuum (white solid). It has the general formula

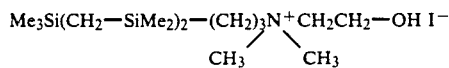

EXAMPLE 11

3g of the compound of Example 6 were charged to a flask diluted in 3g of methanol. N sodium hydroxyde solution was added to raise the pH to 7. The mixture was filtered and stripped to afford as a white solid carbosilane of the formula

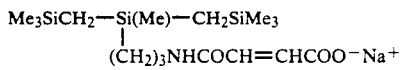

EXAMPLE 12

The aqueous surface activity of several carbosilanes was investigated using a Cham Dyne Surface Tensiometer 5000 and measurements were recorded in conditions as close to equilibrium as possible. The carbosilanes of examples 5 to 10 were mixed with water at different concentrations and their surface activity was measured. In comparison the exemplified carbosilane of G.B. Patent Application 1 520 421 was also tested (Reference). This compound has the formula

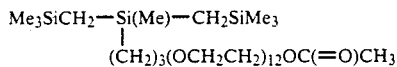

The results are set out in Table I.

TABLE I

| Surface tension of water solutions at 20° C. in Dyne/cm | | | |
|---|---|---|---|
| | Concentration | | |
| Surfactant | 1% | 0.5% | 0.1% |
| Example 5 | 23.5 | 25.3 | 28.5 |
| Example 5a | — | 26.7 | 30.2 |
| Example 6 | 25.4 | 26.3 | 39.5 |
| Example 7 | 23.4 | — | 25.7 |
| Example 7b | 25.0 | 28.7 | 47.5 |
| Example 7c | — | 23.4 | 23.2 |
| Example 8 | 22.9 | 23.1 | 23.4 |
| Example 8b | 24.2 | 25.3 | 29.9 |
| Example 8c | — | 23.3 | 23.5 |
| Example 9 | 23.0 | — | 23.5 |
| Example 10 | 23.5 | 23.8 | 23.6 |
| Example 10b | 23.0 | 28.5 | 52.0 |
| Reference | — | 26.5 | 30.2 |

EXAMPLE 13

The pH stability of several carboxilanes, as prepared in examples set out above, was tested by monitoring the change of the equilibrium surface tension with time, at a concentration which is close to the CMC (critical micelle concentration) i.e. 0.1%, in a series of buffer solutions at pH 2, 4, 10 and 12. The change in surface tension is monitored at 20° C. for 100 hours, and at 50° C. for 170 hours. The results are shown in Table II.

TABLE II

| Surface tension in Dyne/cm at 0.1% in buffer solutions | | | | | | | |
|---|---|---|---|---|---|---|---|
| | | Time (hours) | | | | | |
| | | at 20° C. | | | at 50° C. | | |
| Surfactant | pH | 0 | 24 | 100 | 24 | 72 | 170 |
| Ex. 5 | 2 | 43.2 | 43.8 | 41.0 | 40.3 | — | 41.3 |
| Ex. 7 | 2 | 23.6 | 23.4 | 23.6 | 23.7 | 22.8 | 23.8 |
| Ex. 8 | 2 | 23.0 | 22.9 | 23.3 | 23.0 | 22.3 | 23.0 |
| Ex. 9 | 2 | 22.5 | 22.2 | 23.2 | 23.1 | 22.3 | 23.1 |
| Ex. 10 | 2 | 23.2 | 23.8 | 23.8 | 23.4 | 22.8 | 23.3 |
| Reference | 2 | 30.3 | 30.0 | 29.9 | 31.2 | 29.6 | 31.0 |
| Ex. 5 | 4 | 42.9 | 44.0 | 41.4 | 38.2 | — | 40.9 |
| Ex. 7 | 4 | 26.9 | * | * | * | * | * |
| Ex. 8 | 4 | 23.5 | 23.1 | 23.0 | 23.5 | 22.6 | 23.5 |
| Ex. 9 | 4 | 22.3 | 22.3 | 23.2 | 23.0 | 22.3 | 22.8 |
| Ex. 10 | 4 | 24.9 | 24.9 | 26.1 | 24.8 | 24.1 | 24.7 |
| Reference | 4 | 29.7 | 29.6 | 29.1 | 28.5 | 29.5 | 29.3 |
| Ex. 5 | 10 | 39.6 | 38.8 | 40.5 | 39.9 | — | 39.2 |
| Ex. 7 | 10 | * | * | * | * | * | * |
| Ex. 8 | 10 | 23.7 | 23.4 | 23.1 | 23.2 | 22.1 | 23.3 |
| Ex. 9 | 10 | 22.9 | 22.9 | 23.6 | 22.9 | 22.1 | 22.8 |
| Ex. 10 | 10 | 24.3 | 24.9 | 24.1 | 24.3 | 24.5 | 23.9 |
| Reference | 10 | 29.1 | 30.5 | 30.1 | 27.2 | 29.2 | 30.5 |
| Ex. 5 | 12 | 41.8 | 44.3 | 42.3 | 39.4 | — | 41.3 |
| Ex. 7 | 12 | 24.9 | 24.9 | 26.2 | 25.0 | 24.7 | 23.8 |
| Ex. 8 | 12 | 23.0 | 23.9 | 23.6 | 23.1 | 22.3 | 23.6 |
| Ex. 9 | 12 | 22.8 | 22.5 | 23.8 | 23.2 | 22.1 | 22.9 |
| Ex. 10 | 12 | 23.8 | 24.5 | 23.7 | 23.9 | 22.9 | 23.7 |
| Reference | 12 | 29.3 | 31.2 | 31.4 | 30.2 | 29.2 | 33.0 |

* means that a complexation occurred with phthalates of the buffer solution. thus rendering the results worthless.

EXAMPLE 14

The pH stability of Example 7b, 8b and 10b and of the reference material was tested by following the surface tension changes when the surfactants were dissolved in either a 10% aqueous solution of HCl, or in a 10% aqueous solution of NaOH, during 14 days at room temperature. The results, given in Table III show that the stability in alkaline medium is very good, while a slight deterioration was found after 3 days in acid conditions only for the N-oxide surfactant (Ex. 8b). The reference example showed a deterioration early on.

TABLE III

| Surface tension in Dyne/cm at 0.1% in 10% aqueous solution of HCl and NaOH | | | | | | | |
|---|---|---|---|---|---|---|---|
| | Time (days) | | | | | | |
| Surfactant | 0 | 1 | 2 | 3 | 4 | 7 | 14 |
| in acid | | | | | | | |
| Ex. 7b | 31.1 | 32.1 | 32.2 | 31.3 | 32.7 | 31.5 | 33.1 |
| Ex. 8b | 23.0 | 27.6 | 29.7 | 33.4 | 34.7 | 34.3 | 34.6 |
| Ex. 10b | 28.2 | 26.0 | 25.8 | 25.4 | 25.8 | 26.9 | 28.9 |
| Reference | 30.2 | 32.7 | — | 36.6 | | | |
| in alkali | | | | | | | |
| Ex. 7b | 25.7 | 23.4 | 26.8 | 24.7 | 26.5 | 24.4 | 25.8 |
| Ex. 8b | 22.2 | 22.1 | 23.6 | 22.5 | 23.2 | 22.9 | 23.6 |
| Ex. 10b | 24.4 | 23.5 | 24.6 | 24.0 | 23.9 | 23.7 | 24.4 |

EXAMPLE 15

The pH stability of Examples 5a, 7c and 8c was tested by following the surface tension changes when the surfactants were dissolved in a 5% aqueous solution of HCl during 28 days at room temperature.

TABLE IV

| Surface tension in Dyne/cm at 0.05% in 5% aqueous solution of HCl | | | | | |
|---|---|---|---|---|---|
| | Time (days) | | | | |
| Surfactant | 0 | 5 | 7 | 10 | 28 |
| Ex. 5a | 33.0 | 34.0 | 37.0 | 38.0 | 42.0 |
| Ex. 7c | 26.0 | 26.0 | 25.5 | 25.0 | 25.5 |

TABLE IV-continued

Surface tension in Dyne/cm at 0.05% in 5% aqueous solution of HCl

| Surfactant | Time (days) | | | | |
|---|---|---|---|---|---|
| | 0 | 5 | 7 | 10 | 28 |
| Ex. 8c | 27.0 | 26.5 | 27.0 | 27.0 | 26.5 |

That which is claimed is:

1. An organosilicon compund represented by the general formula

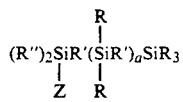

wherein each R is independently selected from alkyl, aryl, halogenated alkyl and halogenated aryl groups having up to 18 carbon atoms, each R' represents an alkylene group separating neighboring silicon atoms by up to 6 carbon atoms, each R" independently deontes R when a is no 0, and when a is 0, is selected from R groups an the group $R_3SiR'$—, Z is selected from hydrophilic substituents containing sulphur, hydrophilic substituents containing nitrogen, hydrophilic substituents containing phosphorus, hydrophilic substituents containing a carboxy-functinal group and hydrophilic substituents containing a salt of a carboxy group and a has the value 0, 1 or 2.

2. An organosilicon compound according to claim 1 wherein at least 80% of the R groups are methyl groups.

3. An organosilicon compound according to claim 1 wherein R' is selected from methylene and dimethylene.

4. An organosilicon compound accoring to claim 1 wherein a is 0 and one R" groups denotes the group —R'SiR₃.

5. An organosilicon compund according to claim 1 wherein Z is selected from groups containing a sulphonate group, groups containing a carboxyl group, groups containing a a zwitterionic group and groups containing a quaternary ammonium salt.

6. An organosilicon compound according to claim 1 wherin Z has the general formula —YQ, wherin Y denotes a divalent group selected from the group consisting of H and C. atoms and N or O atoms and Q is selected from hydrophilic substituents containing sulphur, hydrophilic substituents containing nitrogen, hydrophilic substituents containing phosphorus and hydrophilic substituents containing a carboxy-functinal group and hydrophilc substituents containing a salt of said carboxyl group.

7. An organosilicon compund according to claim 1 wherein Z denotes the group

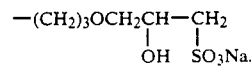

8. An organosilicon compound according to claim 1 wherein Z is selected from the groups —(CH₂)₃NHCOCH=CHCOOH, —(CH₂)₃NHCOCH=CHCOO⁻Na⁺ and

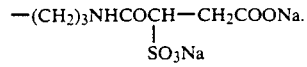

9. An organosilicon comound according to claim 1 wherein Z denotes the group

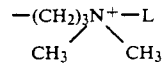

wherein L is selected from $(CH_2)_3SO^-_3$, $O^-$, $CH_3I^-$ and $CH_2CH_2OH$ $I^-$.

10. A method of making organosilicon compounds of the general formula

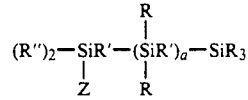

wherein each R is independently selected from alkyl, aryl, halogenated alkyl and halogenated aryl groupshaving up to 18 carbon atoms, each R' represents an alkylene group separating neighbouring silicon atoms by up to 6 carbon atoms, each R" independently denotes R when a is not 0, and when a is 0, is selected from R groups and the group $R_3SiR'$—, Z is selected from hydrophilic substituents containing sulphur, hydrophilic substituents containing nitrogen, hydrophilic substituents containing phosphorus, hydrophilic' substituents containing a carboxy-functional group adn hydrophilc substituents containing a salt of a carboxyl group and a has the value 0, 1 or 2, which comprises reacting together a hydrophilic substituent containing compound Z' with a silalkylene compound of htegeneral formula

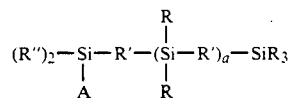

wherein R, R', R" and a are as defined above and A is selected from the group consisting of a hydrogen atom adn a reactive group and Z' denotes a group such that upon reaction of A with Z' the group Z is formed.

11. A method according to claim 10 wherein A is selected from H, an amino-containing group and an epoxy-containing group.

12. A method according to claim 10 wherein A is a hydrogen atom and Z' has an unsaturated group.

13. A method according to claim 12 wherein Z' has the general formula A'Q, wherein A' is selected from an allylene and a vinylene group and Q is selected from hydrophilic substituents containing sulphur, hydrophilic substituents containing nitrogen, hydrophilic substituents containing phosphorus, hydrophilic substituents containing a carboxy-functional group and hydrophilic substituents containing a salt of a carboxyl group.

14. A method according to claim 12 wherein is carried out in the presence of an addition reation catalyst which is a Pt containing compound.

15. A method according to claim 10 wherein A is an aminofunctional group and Z' is selected from an acid anhydride, a sultone, hydrogen peroxide, a haloalkane and a halocarbinol.

16. A method according to claim 10 wherein A is an epoxyfunctional group and Z' is a sulphite.

17. A method according to claim 10 wherein A contains a carboxylic group and Z' is a sulphite.

* * * * *